United States Patent [19]

Karsay et al.

[11] 4,260,846
[45] * Apr. 7, 1981

[54] CONTINUOUS CYCLIC PROCESS FOR ALKYLATION OF HYDROCARBONS

[75] Inventors: Bela I. Karsay, DeWitt; Robert L. Sturtevant, Baldwinsville; Alan B. Gancy, Syracuse, all of N.Y.

[73] Assignee: Allied Chemical Corporation, Morris Township, Morris County, N.J.

[*] Notice: The portion of the term of this patent subsequent to Apr. 10, 1996, has been disclaimed.

[21] Appl. No.: 47,448

[22] Filed: Jun. 11, 1979

Related U.S. Application Data

[63] Continuation-in-part of Ser. No. 863,655, Dec. 23, 1977, abandoned.

[51] Int. Cl.³ .............................................. C07C 2/58
[52] U.S. Cl. .................................... 585/730; 585/731
[58] Field of Search ............................... 585/730, 731

[56] References Cited

U.S. PATENT DOCUMENTS

| | | | |
|---|---|---|---|
| 2,435,402 | 2/1948 | McAllister et al. | 585/731 |
| 2,437,091 | 3/1948 | Goldsby et al. | 585/730 |
| 4,148,836 | 4/1979 | Sturtevant et al. | 585/731 |

Primary Examiner—Curtis R. Davis
Attorney, Agent, or Firm—Thomas D. Hoffman

[57] ABSTRACT

An improved cyclic process for the alkylation of isoparaffins with olefins in the presence of a circulating concentrated sulfuric acid catalyst is disclosed. Improvement in the octane rating of the product alkylate is achieved by periodic fortification of the sulfuric acid catalyst with a sulfur trioxide-bearing fortifying agent under conditions wherein the harmful effects caused by contact of the sulfur trioxide with the hydrocarbons in the alkylation zone are minimized. The acid catalyst is fortified during less than about 15% of the cycles of the circulating acid catalyst through the alkylation system to maintain the water content of the acid catalyst in the range of above about 1% and below about 4% by weight. The process effects not only essentially 100% utilization of the fortifying agent for water removal but also improves the octane rating of the product alkylate while simultaneously extending the service life of the acid catalyst by allowing use of the catalyst having higher organic content.

4 Claims, 1 Drawing Figure

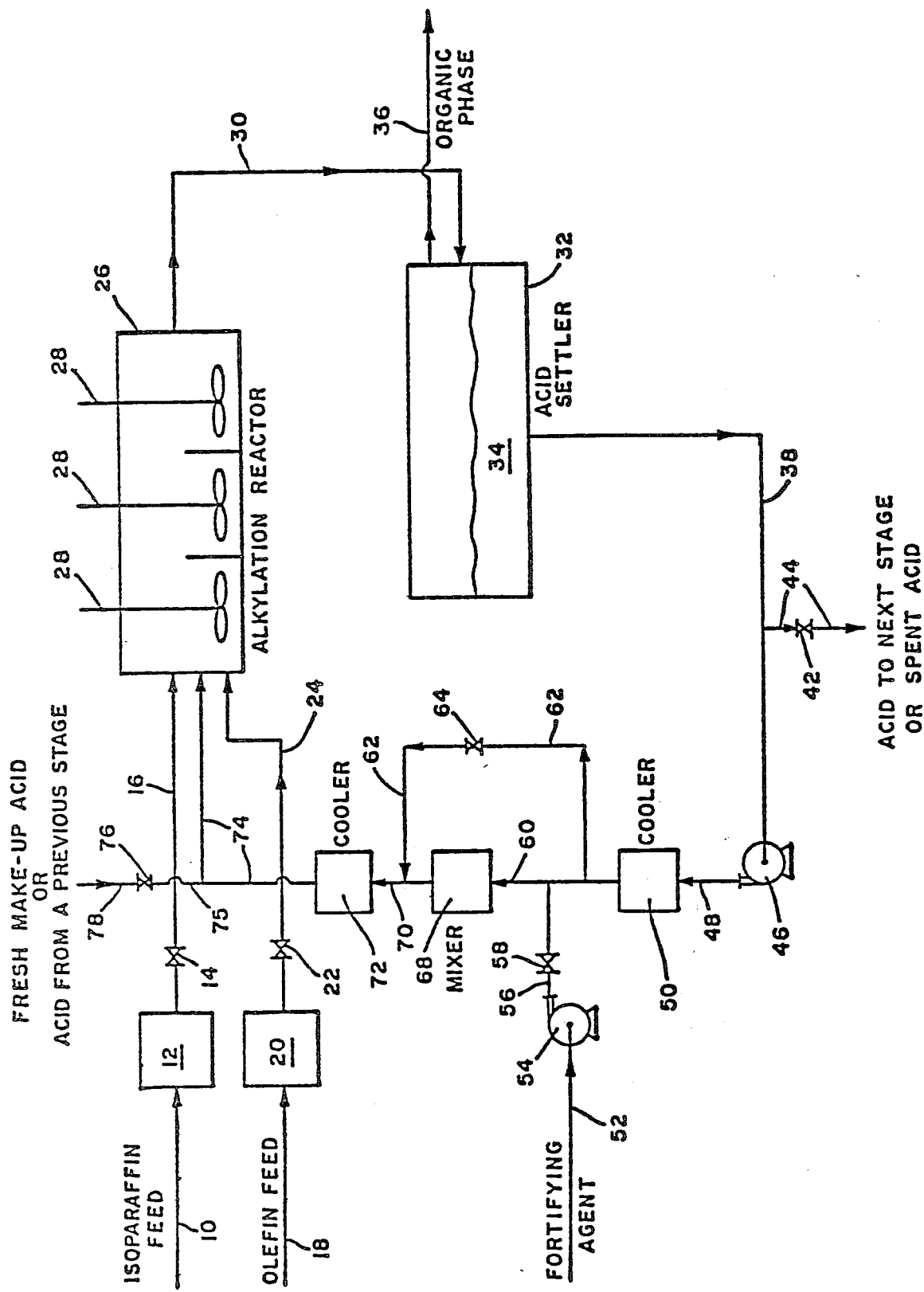

CONTINUOUS CYCLIC PROCESS FOR ALKYLATION OF HYDROCARBONS

CROSS-REFERENCE TO RELATED APPLICATION

This application is a continuation-in-part of copending application Ser. No. 863,655, filed Dec. 23, 1977, and now abandoned.

BACKGROUND OF THE INVENTION

This invention relates to a process for fortifying the sulfuric acid catalyst used as an alkylation catalyst in the production of premium grade (high octane number) gasoline by the petroleum industry. More particularly, this invention relates to the periodic fortification of the alkylation acid to increase the octane rating of the product alkylate and to prolong the catalytic effectiveness of the sulfuric acid.

It is common practice in petroleum refineries to treat low boiling isoparaffins or alkanes with alkylating reagents such as olefins, in the presence of a sulfuric acid catalyst to produce a high octane alkylate, boiling in the gasoline range. It is well know that the sulfuric acid catalyst does not undergo major chemical change during the alkylation process but the acid concentration diminishes due to the build-up of water and organic impurities and red oils which originate from undesired side reactions. As the build-up of these diluents approaches 10–12%, the concentration of the alkylation acid is reduced from its original value of about 98.0–99.5% to about 88–90%. At these lower concentration values, the catalytic activity of the alkylation acid is decreased and the octane number of the product alkylate is undesirably lower. At this point all the alkylation acid must be withdrawn from the system and reprocessed by regeneration. In reprocessing, the spent acid is usually thermally decomposed to sulfur dioxide, carbon dioxide and water. After purification, the sulfur dioxide generated is reconverted to sulfuric acid by the conventional contact process.

Besides the fuel and energy required to regenerate the acid, another obvious disadvantage of this widely used destructive regeneration process is that the spent acid, consisting mostly (88–90%) of sulfuric acid, is completely decomposed to eliminate the relatively small amounts (10–12%) of water and organic impurities. Analyses of spent or used alkylation acid vary somewhat depending on the operating conditions.

DESCRIPTION OF THE PRIOR ART

In an attempt to overcome the above difficulties and extend the effective service life of the alkylation acid, numerous investigations have been directed to understanding the operating variables of the alkylation process which affect the alkylate quality. The importance of a high acid concentration and the maintenance of a constant water content in the alkylation acid is disclosed by U.S. Pat. No. 2,242,845. In the specification of this U.S. patent, it has been proposed that more concentrated sulfuric acid, for example 98–103% $H_2SO_4$, be used as the make-up acid to maintain the strength of the alkylation acid between a concentration of about from 88.0% to 95% and preferably to 91% by weight $H_2SO_4$. Alternately, it is disclosed that partially spent acid may be withdrawn from the system and the above concentration range be maintained by fortification with $SO_3$ or fuming sulfuric acid.

U.S. Pat. No. 2,437,091 discloses that free $SO_3$, which rapidly attacks the hydrocarbons in the alkylation acid, and water, which is built-up in the system by side reactions during the alkylation, are deleterious both to the alkylate quality (octane number) and the effective service life time of the alkylation acid. In this U.S. Pat. No. 2,437,091, it is proposed that part of the alkylation acid be continuously discharged and the balance prechilled and thence continuously fortified with fuming $H_2SO_4$ or $SO_3$ to maintain a water content in the system below 4% by weight and preferably below 1% by weight.

In U.S. Pat. No. 2,465,049, $SO_3$ or fuming $H_2SO_4$ is continuously applied to the alkylation acid and hydrocarbon feedstocks in a mixter immediately before the alkylation zone to dehydrate the feeds and to convert the water content therein to additional $H_2SO_4$ catalyst. A slight excess of a $SO_3$ fortifying agent, over that required to react with the water in the hydrocarbon feeds, is applied to remove the water generated by side reactions within the alkylation zone.

In spite of these investigations of the alkylation process, it is still recognized by the petroleum industry that a practical fortification process is needed.

It is an object of the present invention to provide a process for maximizing the octane rating of alkylate product and simultaneously improving the alkylate yield.

It is another object of this invention to provide a process for reducing the rates of water and organic impurities built-up in the alkylation acid.

It is a further object of this invention to provide a process for fortifying the alkylation catalyst with $SO_3$ agents under conditions which minimize the exposure of the fortifying agents to the organic matter dissolved in the acid catalyst.

Still another object of this invention is the extension of the effective service life time of the acid catalyst and the reduction in the quantity of spent acid subjected to destructive regeneration.

SUMMARY OF THE INVENTION

The present invention involves an improvement in a continuous cyclic process for producing alkylate wherein an alkylatable hydrocarbon is contacted with an alkylating agent in an alkylation system under alkylation conditions in the presence of a circulating concentrated sulfuric acid catalyst containing above about 1 weight % and below about 4 weight % of water; the reaction mixture so produced is separated into alkylate and alkylation acid catalyst; a portion of the alkylation acid catalyst is cooled and recycled to the alkylation system; and the water content of the circulating alkylation acid catalyst is reduced by addition thereto of a sulfur trioxide fortifying agent. The improvement comprises continuously maintaining the water content in the circulating alkylation acid catalyst in the range of above about 1 weight % and below about 4 weight % by periodically introducing a sulfur trioxide fortifying agent into the cooled portion of the circulating alkylation acid catalyst during less than about 15% of the cycles of the circulating alkylation acid catalyst through the alkylation system.

In an alternate embodiment of the present invention wherein the periodic fortification by a sulfur trioxide fortifying agent is effected during less than about 15% of the cycles of the circulating alkylation acid through the alkylation system, the water content of the circulating alkylation acid is maintained in the range above about 1.0% and below about 4% by weight by extending the duration of each periodic application over 2 to 3 successive cycles of the circulating alkylation acid through the alkylation system.

In a preferred embodiment, the water content in the circulating alkylation acid is maintained above about 1.5 weight % and below about 2.5 weight % by periodically introducing a $SO_3$ fortifying agent into the circulating alkylation acid during less than about 3% of the cycles of the circulating alkylation acid through the alkylation system.

The present invention provides an improved continuous cyclic process wherein, by periodic application of a sulfur trioxide fortifying agent to the circulating acid catalyst during less than about 15% of the cycles of the acid through the alkylation system, the following advantages are realized: (a) maintenance of the water content of the circulating acid catalyst within the range above about 1% and below about 4% by weight; (b) extension of the catalyst service life time for producing high quality alkylate even up to an acid catalyst organic content of at least about 10 weight %, (c) an improved octane rating for the alkylate, over the entire acid catalyst service lifetime, of at least about 91; and (d) essentially complete utilization of the sulfur trioxide fortifying agent for water removal from the acid catalyst.

By operating in accordance with this invention the $SO_3$ is essentially completely utilized by reaction only with the water content of the sulfuric acid catalyst and very little, if any $SO_3$, either as free $SO_3$ or as pyrosulfuric acid, $H_2S_2O_7$, is recycled to the alkylation system wherein harmful side reactions with the hydrocarbon feeds can occur. By specific periodic application of the fortifying agent in accordance with the present invention, the water content of the acid is allowed to vary somewhat between above about 1 weight % and below about 4 weight %, without adverse effects; this is contrary to the heretofore generally accepted practice of maintaining substantially constant water content in the alkylation acid. It has been discovered, unexpectedly, that by maintaining a constant water content, especially a water content below about 1% as suggested by the prior art, the build-up rates of water, organic impurities and red oils are accelerated and the catalytic activity of the alkylation acid is rapidly diminished. With a less active catalyst, the octane number of the product alkylate becomes unacceptably low and alkylation acid has to be discharged for regeneration. However, in accordance with the present invention, the water content in the circulating acid is maintained within a range of above about 1% to below about 4% by weight, preferably above about 1.5% to below about 2.5% by weight and a higher final organic content can be tolerated in the alkylation acid catalyst while producing alkylate having an octane rating of at least about 91. While the prior art teaches that the organic matter is a less harmful diluent in the alkylation acid than water, only the present invention discloses a cyclic process of repeatedly applying fortifying agents, at definite intervals, whereby the water content of the circulating acid catalyst is maintained within the above-described range so that the alkylation acid catalyst having high organic content, e.g., at least about 10 weight % is effective in producing alkylate of higher octane than previously thought possible.

In accordance with the present invention, there is provided a process for the periodic fortification of the sulfuric acid catalyst for the alkylation of hydrocarbons which comprises an alkylation system wherein alkylatable $C_4$-$C_5$ isoparaffin feed stock is contacted with alkylating agent ($C_2$-$C_5$ olefins) in the presence of a circulating concentrated sulfuric acid catalyst containing at least about 1% but less than about 4% by weight water, under alkylation conditions in an alkylation reactor equipped with agitators, and wherein the alkylation product (alkylate) is separated from the acid catalyst, a portion acid catalyst is cooled and recycled to the alkylation system, and wherein the water content of the circulating alkylation acid is maintained within the range of more than about 1% but less than about 4%, preferably above about 1.5% to below about 2.5% by weight, by periodically introducing a $SO_3$-bearing fortifying agent into the circulating alkylation acid catalyst, the periodic introduction being effected during less than 15% of the cycles of circulating acid catalyst through the alkylation system. During a large portion of the alkylation operation the acid is circulated through the system without the addition of the fortifying agent to allow the water content to vary within the range, described above. Then, a predetermined amount of a $SO_3$-bearing fortifying agent, e.g., 0.1 to 65% oleum, is added with good agitation and cooling to at least a portion of the circulating alkylation acid; the remainder is discharged or transferred to another alkylation system. The amount of circulating acid discharged is determined by level of organic impurities built up between applications of the fortifying agent. By fortifying periodically and extending the duration of the fortification over at least one but no more than three cycles such that the $SO_3$-bearing fortifying agents are applied in less than about 15% of the cycles of the circulating alkylation acid through the alkylation system, the exposure of the active ingredients in the fortifying agents to the hydrocarbons in the alkylation acid is minimized. When fortification was applied in accordance with the present invention, the water and organic build-up rates are found considerably lower than in experiments where the same quantity of fortifying agent is applied continuously.

For purposes of this invention, the term "cycle" represents the equivalent of one passage of the entire alkylation acid volume or inventory through an alkylation system having at least a single alkylation reactor or stage; this stage can conveniently be part of a multistage alkylation unit.

When reference is made herein to percent of the cycles of the circulating alkylation acid catalyst is passed through the alkylation system, it is to be understood that this is in reference to one hundred complete cycles. For example, if the fortifying agent is applied every second cycle this would be fortification in 50% of the cycles of the circulating alkylation acid catalyst through the alkylation system; once every hundred cycles would be 1% of the cycles. In an example wherein the fortifying agent is applied every 50 cycles and the duration of the application is extended over three successive cycles, this would be fortification in 3 cycles out of 52, 6 cycles out of 104 cycles of the circulating alkylation acid through the alkylation system and thus there would be fortification during less than about 5.8% of cycles of the circulating alkylation acid through the alkylation system.

BRIEF DESCRIPTION OF THE DRAWING

The present invention is more clearly illustrated in the attached drawing. FIG. I is a schematic view of a single stage alkylation unit incorporating the principles of the present invention.

DETAILED DESCRIPTION OF THE INVENTION AND OF THE PREFERRED EMBODIMENTS

Referring to FIG. 1, liquified $C_4$–$C_5$ isoparaffin feed from line 10, after passing through a suitable drier 12 and valve 14 is introduced under pressure via line 16 into alkylation reactor 26, equipped with agitators 28. Reactor 26 may be any conventional or other suitable type of reactor. The liquefied olefin feed, which may be a mixture of $C_2$ to $C_5$ olefins from a refinery cracking unit (not shown), is passed under pressure through line 18 and a suitable drier 20 and thence through valve 22 which regulates the flow through line 24 into the stirred alkylation reactor 26. Valves 14 and 22 are regulated to adjust the molar ratio of isobutane to olefin in the feed to 4–10:1, preferably 4–7:1. The olefin and isoparaffin feeds supplied to reactor 26 may advantageously be caustic-washed and then water-washed. While predrying of the hydrocarbon feeds is the preferred procedure, it is to be understood that this is not essential.

Fresh make-up acid or alkylation acid catalyst from a previous alkylation system or stage of a multisgate alkylation unit (not shown) is introduced into line 75 from line 78 via valve 76 and thence to reactor 26 via line 74. The amount of make-up acid or alkylation acid catalyst is equal to the amount withdrawn and not recycled. In this way, the organic impurities are reduced.

The acid catalyst is maintained at a temperature below 25° C., before introduction to reactor 26. Generally, the acid catalyst is contacted with the hydrocarbon feeds in the alkylation reactor for an average period of time of at least 5 minutes and not more than 20 minutes. The alkylation mixture is stirred at a temperature between 10° and 20° C., preferably 10° C. This temperature may be maintained by the partial evaporation of the volatile hydrocarbon phase. Heat generated in the alkylation reactor 26 can also be removed by suitable heat exchangers (not shown). The alkylation reaction mixture is discharged from reactor 26 by line 30 and introduced into acid settler 32. Herein separate organic and acid phases are formed, and the separated organic phase is removed by line 36 for passage to suitable equipment for caustic washing and water washing and thence to fractionation towers (not shown). The isoparaffin recovered via fractionation can be recycled to line 10.

The acid layer 34 in settler 32 is continuously removed from settler 32 via line 38. A portion of the acid catalyst, which is approximately equivalent to the volume of make-up acid or acid added from a previous stage into line 75 via line 78 and valve 76, is continuously withdrawn from line 38 via line 44 through valve 42. The remainder of the acid catalyst passes through pump 46 and line 48 to a suitable cooler 50 wherein the temperature is reduced to below about 25° C., generally between 20° and 25° C. The cooled recycle acid then flows through line 60 into which is periodically introduced, by line 56 through valve 58, a predetermined amount of a $SO_3$ fortifying agent. Any commercially available $SO_3$ fortifying agent can be used if applied in accordance with the present invention. Sulfuric acid brought to 100% by the addition of $SO_3$ to concentrated sulfuric acid as well as various oleums (13%, 16%, 20%, 30% and 65%) and 100% liquid $SO_3$ are suitable. Liquid $SO_3$, containing stabilizers, is preferably treated to separate the stabilizers before use. For this reason oleum or nonstabilized $SO_3$ are preferred. When an amount of fortifying agent necessary to reduce the water content to the desired concentration is periodically added to the recycle acid catalyst at a temperature between 20° and 25° C., e.g., continuously during at least one to no more than three successive cycles, with good agitation in mixer 68, the fortifying agent is uniformly distributed throughout the entire acid inventory and no harmful effects are observed. In contrast, the continuous (see TABLE I, below) as opposed to periodic, as described herein (see TABLE II, below) addition of $SO_3$ fortifying agents can cause a rapid build-up of water and acid soluble, high molecular weight organic matter and may require discharge and regeneration of such spent alkylation catalyst. Regeneration reactions may lead to the formation of solid carbonaceous materials or tarlike products. Such reactions are often accompanied by a substantial evolution of $SO_2$. These harmful effects are obviated when fortifying agents are applied periodically as described hereinabove, and the duration of the periodic addition is extended over at least one, preferably at least one to no more than three successive passages of recycled acid in accordance with the present invention. During the passages (cycles), when the acid catalyst is not being fortified, mixer 68 can be bypassed via line 62 and valve 64.

The fortified recycle acid is passed from the mixer 68 through line 70 to cooler 72 wherein heat generated by the reaction of $SO_3$ with the water content of the recycle acid is removed. The $SO_3$, which may be present as pyrosulfuric acid, $H_2S_2O_7$, reacts exothermically with water dissolved in the bulk recycle acid. The reaction tends to reach completion with agitation in mixer 68 and therefore only small amounts, if any, free $SO_3$ is introduced into the alkylation reactor 26. Because the fortifying agent is added during less than 15% of the cycles the circulating acid through the alkylation system, any $SO_3$ that is introduced into the reaction will only be so introduced in 15% of the cycles. Further, when the duration of the periodic application is extended over at least one, preferably at least one to no more than three successive cycles, only 30–50% of the $SO_3$ required to react with the water content of the acid catalyst is introduced in any single passage of the acid recycled through the alkylation zone. Thus, the $SO_3$ is essentially completely utilized by reaction only with the water content of the acid and little, if any free $SO_3$, or $H_2S_2O_7$, is recycled to the reactor 26 wherein harmful side reactions with the hydrocarbon feeds could occur. Application of the fortifying agent according to the present invention results in a higher yield of alkylate of higher octane number and lower build-up rates for organic impurities and water than previously thought possible. Thereby the service life of the acid catalyst is longer and the quantity of make-up acid lower.

It has been found that the water content of the acid can vary over a wider range than previously thought acceptable. In accordance with the present invention the water content of the acid catalyst can be maintained within the optimum range of more than about 1 to less than about 4%, preferably more than 1.5 to less than about 2.5%. It has also been discovered that, by periodic application of $SO_3$ fortifying agents according to the present invention, the sulfuric acid is an efficient catalyst at a higher organic content than previously used.

The amount of $SO_3$ required to return the acid to the optimum water content of between above about 1 and below about 4%, preferably about 1.5 to about 2.5%, is conveniently determined by monitoring the circulating acid. It is understood that line 52 will be equipped with a suitable flow meter, so that the desired predetermined amount of $SO_3$ required to react with the water content of the acid catalyst can be easily ascertained from the velocity of flow of the $SO_3$ fortifying agent and the $SO_3$ concentration therein as well as the amount of water in the acid catalyst.

When a predetermined amount of fortifying agent is applied in accordance with the present invention, an approximately equal volume of alkylation acid is discharged via line 44. The amount of organics in the sulfuric acid are maintained within the desired range by periodically discharging acid from line 44 through valve 42 when there is fortification.

The following Examples further illustrate the present invention and set forth the best mode presently contemplated for its practice.

EXAMPLES 1–12

Examples 1–12 illustrate alkylations using butene-1 as the olefin feed and isobutane or isopentane as the isoparaffin feed. This is not to be considered limiting space similar results are obtained with the other olefins encountered in commercial alkylation processes, such as ethylene, butene-2, isobutylene, propylene and amylenes. Fresh (make-up) sulfuric acid, 98.0 to 99.8%, generally 99.0%, ash free, was charged into one stage of a multistage alkylation reactor similar to the one described in FIG. I above. A stream of dried, liquefied isobutane and olefin in the molar ratio of 4:1 to 10:1, generally 4:1 to 7:1, was introduced into the reactor until the sulfuric acid to hydrocarbon volume ratio was about 60:40 to 55:45. It is well known that the sulfuric acid must be in excess to operate as an effective alkylation catalyst. The two liquid hydrocarbons, and acid were mixed with a high speed agitator in the reactor to disperse the hydrocarbons in the acid, and to allow the alkylation reaction to take place. Alkylations were generally conducted at temperatures between 10° and 20° C. and under pressure (40–80 psi) so that the hydrocarbons which were gases under ambient conditions are in liquid form in the alkylation reactor. The reactor can be immersed in a cooling bath to remove the heat generated by the alkylation reaction.

When the recycle acid was fortified, in accordance with the present invention with 0.1–65% oleum, or liquid $SO_3$, the fortifying agent was applied under somewhat higher pressure than the rest of the system, via line 52, pump 54 and line 56 and regulating valve 58 into the recycle acid stream passing through line 60.

While oleum of any strength may be applied with equal success in accordance with this invention, economic considerations may make the use of 13–30% oleum preferable.

Results of Examples 1–7 are given in Tables I and II, below. Unless otherwise indicated percent is by weight.

EXAMPLE 1

This was a simulation of a one stage alkylation process without fortification in one stage of a multistage unit and wherein both the water and organic content of the acid were allowed to build-up unimpeded.

The initial acid charge was 3,500 g (1,900 mls) of 99.8% sulfuric acid, which was passed (cycled) 450 times through the alkylation reactor. The hydrocarbon feed was a 10:1 molar mixture of isobutane and butene-1. Feeding rate of acid was 36 cc/min, while that of the hydrocarbon mixture 24 cc/min. Average retention time in the reactor, which had a volume of 300 cc, was 5 minutes.

Acid samples were taken at frequent intervals: initially after every 5 cycles, later after every 50–100 cycles. The samples were analyzed for total acidity, free $H_2SO_4$, water and carbon contents. The difference between total acidity and free $H_2SO_4$ represented the percent of alkyl acid sulfate and aryl sulfonates present. Alkylate samples were taken about the same time as the acid samples, and were analyzed by a gas chromatograph for composition. The octane number (O.N.) was calculated, in the standard way, from the composition.

Results of the analyses have been summarized in Table I. From the % $H_2O$ and % C values in Table I, the build-up rates of water and organic impurities in various periods of the alkylation run have been calculated, and the results per 100 cycles have been listed in Table II, below. The percentages of impurities, as discussed above, covered the range normally found in a conventional alkylation. The fluctuations in the build-up rates of the diluents have been discovered in the course of this study.

TABLE I

Build-up of Water and Organic Impurities in Alkylation Acid in a Conventional Alkylation Process (Using No Fortification)

| Cycles Completed | % Titratable Acidity | % Free $H_2SO_4$ | % $H_2O$ | % C | O.N. of Alkylate |
| --- | --- | --- | --- | --- | --- |
| 0 | 99.8 | 99.8 | 0.2 | 0.0 | — |
| 20 | 96.4 | 95.3 | 0.9 | 1.2 | 94.2 |
| 25 | 96.5 | 95.5 | 0.8 | 1.4 | 94.4 |
| 50 | 95.7 | 94.8 | 1.3 | 1.8 | 94.6 |
| 100 | — | — | 1.7 | 2.5 | 95.0 |
| 150 | — | — | 2.1 | 3.5 | 95.1 |
| 200 | — | — | 2.4 | 3.9 | 94.6 |
| 400 | — | — | 3.4 | 6.0 | 92.0 |
| 450 | 89.3 | — | 4.0 | 6.7 | 91.4 |

EXAMPLE 2

This was a demonstration of a one stge fortification process of the prior art, wherein the alkylation acid was continuously fortified, cooled and forwarded to the alkylation reactor.

The initial acid charge was 1860g (1016 cc) 98.0% $H_2SO_4$. All other conditions were the same as in Example 1. The acid was cycled 300 times through the alkylation reactor. During each passage of the acid through the system, a continuous stream of 65% oleum was added, with good agitation and cooling, in a quantity to maintain the water content of the acid at 2%. Acid samples were withdrawn and analyzed on a regular basis. The build-up rates per 100 cycles of water and organics in the acid were 3.0% and 2.8% respectively.

EXAMPLE 3

This was a demonstration of the effect of the frequency of periodic fortification on the rates of buildup of water and organic impurities in the alkylation acid. The starting acid was 98% $H_2SO_4$. The pressurized acid was circulated continuously through the system and the water content was allowed to vary from about 1.6 to 2.2 percent by weight of the alkylation acid. After the completion of 5 passages of the alkylation acid through reactor 26, the required amount of 30% oleum was added, with good agitation, during one cycle to reduce the water content of the alkylation acid to 1.6 to 2.0 percent. All other conditions were the same as the Example 1.

EXAMPLE 4

This Example was similar to Example 3 except that the required amount of 30% oleum was added to the circulating alkylation acid during one cycle at intervals of every 10 cycles, i.e., 10% of the cycles of the alkylation acid through the alkylation reactor.

EXAMPLE 5

This Example was similar to Example 3 except that the required amount of 30% oleum added during one cycle, at intervals of every 15 cycles, i.e., 6.6% of the cycles of the alkylation acid through the reactor 26. The water and organic build-up rates were found considerably lower in runs 4 and 5 wherein the fortifying agent was added less frequently than in run 2 wherein the fortifying agent had been added continuously.

EXAMPLES 6-7

To find the optimum frequency for the fortification, the acid initially b 98.5% $H_2SO_4$, was circulated through the system for 30 and 50 cycles before fortifying agent was applied. When the water content in alkylation acid was measured to be 0.2 to 0.3% above its initial value, the predetermined amount of 30% oleum was added, with good agitation, during one cycle. The water and organic buildup rates (see Table II, below) were found to be considerably lower than in Example 3 where the same quantity of fortifying agent had been added more frequently. The water content was allowed to vary from 1.5 to 1.8% by weight in the alkylation acid.

TABLE II

Effect of Frequency of Fortification on the Build-up Rates of Water and Organic Impurities in the Alkylation Acid

| Example | Frequency of Fortification[1] | Build-up Rates per 100 passages of acid[2] Water | Build-up Rates per 100 passages of acid[2] Org. Impurities | O.N.[3] of Alkylate after 200 cycles | O.N.[3] of Alkylate after 400 cycles |
|---|---|---|---|---|---|
| 1 | none | .84[4] | 1.5[4] | 94.6 | 92.0 |
| 2 | continuous | 3.0 | 2.8 | 94.2 | —[5] |
| 3 | 20% | 3.3 | 3.3 | 93.3 | —[6] |
| 4 | 10% | 1.0 | 2.0 | 94.8 | 92.4 |
| 5 | 6% | 0.9 | 2.0 | 95.0 | 92.5 |
| 6 | 3% | 0.6 | 1.6 | 94.9 | 93.4 |
| 7 | 2% | 0.6 | 1.6 | 94.8 | 93.5 |

[1] Expressed as percent of the time the acid catalyst was in contact with the hydrocarbons.
[2] Increase in weight, of water and organic impurities per 100 g of alkylation acid per 100 passages of acid through the alkylation zone.
[3] Octane Number.
[4] Average values per 100 g of alkylation acid per 100 passages of alkylation acid through the alkylation system (Calculated from data in Table I).
[5] The O.N. of alkylate was less than 91 after 300 cycles and alkylation acid was discarded.
[6] The O.N. of alkylate was less than 91 after 250 cycles and alkylation acid was discarded.

A comparison of the results of the first two examples (see Table II, above) showed that the rate of water build-up in a continuous fortification (Example 2) was about 3.6 times higher than in an alkylation (Example 1) wherein no fortification was employed. The corresponding carbon build-up rate was about twice as high as wherein the acid was not fortified. As was evident in Table II when the fortifying agent was added 20% of the time (Example 3), the build-up rates of water and organics were essentially identical to the rates obtained in a continuous fortification process (Example 2). These build-up rates were considerably lower in Examples 4-7, wherein the fortifying agent was applied less frequently, in accordance with the present invention.

EXAMPLE 8

This Example illustrated the operation of a one stage prior art alkylation process wherein a portion of the alkylation acid was discharged continuously and an approximately equal volume of fresh make-up acid was simultaneously added to the system. The build-up rates of the water and organic impurities (organics) in the alkylation acid which had a water content of 3.7% by weight were 0.6 and 1.4% by weight, per 100 cycles, respectively. The octane number (O.N.) of the alkylate produced was 92.2. The results of a detailed analysis of the components of the system have been given in Table III, below. Other experimental conditions were the same as detailed in Example I, above.

TABLE III

Analyses of the Sulfuric Acid Catalyst* in One Cycle of a Conventional Alkylation Process of the Prior Art (Water Content at 3.7%)

| Composition of Alkylation Acid | Acid In weight in lbs. | Acid In % by weight | Acid Out weight in lbs. | Acid Out % by weight | Acid Discharged weight in lbs. | Fresh or makeup-Acid Added weight in lbs. | Fresh or makeup-Acid Added % by weight | Acid in Next Cycle weight in lbs. | Acid in Next Cycle % by weight |
|---|---|---|---|---|---|---|---|---|---|
| $H_2SO_4$ | 100.000 | 90.000 | 100.000 | 89.984 | 0.200 | .200 | 99.010 | 100.000 | 90.000 |
| $H_2O$ | 4.111 | 3.700 | 4.117 | 3.705 | 0.008 | .002 | 0.990 | 4.111 | 3.700 |
| Organics | 7.000 | 6.300 | 7.014 | 6.311 | 0.014 | .000 | 0 | 7.000 | 6.300 |

*also called alkylation acid

EXAMPLE 9

This Example illustrated the operation of a one stage prior art alkylation process wherein a portion of the alkylation acid was discharged and, at the same time, the remainder was condinuously fortified with 100%, $SO_3$ and 98.973% $H_2SO_4$ was used as make-up acid. The build-up rates of water and organic impurities (organics) in the alkylation acid which had a water content of 0.5% by weight were respectively, 3.5% and 6.0% by weight, per 100 cycles. The octane number (O.N) of the alkylate produced was 92.2. The detailed analyses of the components of the system have been given in the Table IV, below. Other experimental conditions were the same as described above.

above. The octane number of the product alkylate was 92.2. Results have been given in Table VI, below. This process was repeated every 63 cycles, for 441 cycles of the circulating alkylation acid through the alkylation zone.

EXAMPLE 12

TABLE IV

Analysis of the Sulfuric Acid Catalyst in One Cycle of a Continuous Fortification Process of the Prior Art (Water Content at 0.5%)

| Composition of Alkylation Acid | Acid In | | Acid Out | | Acid Discharged | Fresh or makeup-Acid Added | | Fortifying Agent added | | Acid in Next Cycle | |
|---|---|---|---|---|---|---|---|---|---|---|---|
| | weight in lbs. | % by weight | weight in lbs. | % by weight | weight in lbs. | weight in lbs. | % by weight | weight in lbs. | % by weight | weight in lbs. | % by weight |
| $H_2SO_4$ | 100.000 | 88.500 | 100.000 | 88.426 | 0.480 | .289 | 98.973 | — | — | 100.000 | 88.500 |
| $H_2O$ | 0.565 | 0.500 | 0.600 | 0.530 | 0.003 | .003 | 1.027 | — | — | 0.565 | 0.500 |
| Organics | 12.429 | 11.000 | 12.489 | 11.044 | 0.060 | .000 | 0 | — | — | 12.429 | 11.000 |
| $SO_3$ | — | — | — | — | — | — | — | 0.156 | 100.000 | | |

EXAMPLE 10

This Example illustrated a preferred embodiment of a one stage fortification process of the present invention wherein the octane number of the product alkylate was maximized. The alkylation acid was circulated through the alkylation reactor for 63 cycles. The water content increased from 1.5% to 2.0% by weight; the organic content increased from 3.5% to 4.0% by weight. In the 63rd cycle, the water in the alkylation acid was returned to 1.5% by applying 100% $H_2SO_4$ in one cycle. Concurrent with the application of the fortifying agent, an approximately equal volume of alkylation acid was discharged sufficient to return the organic content therein to about 3.5% by weight. The results have been detailed in Table V, below. The build-up rates of water and organic impurities in the alkylation acid which had a water content of 1.5% by weight were, respectively, 0.8% and 1.6% by weight, per 100 cycles. The octane number of the recovered alkylate was 95.1. These fortification and discharge processes were repeated every 63 cycles, i.e. about 1.6% of the cycles of the circulating acid through the system.

This Example is an alternate embodiment of the invention illustrated in Example 11, wherein the duration of the periodic application of the fortifying agent is extended over no more than 3 successive cycles. The water in the alkylation acid is allowed to increase to about 2.0 weight %. Then after 63 cycles, the water content is returned to 1.5% by applying 13% oleum over three successive cycles. The organic content in the acid is maintained at 8.5% by the method described in Example 10. The build-up rates of water and organic impurities are essentially the same as in Example 10, above. This process is repeated every 63 cycles, e.g. in cycles 128–130, 193 to 195 and so forth until 455 cycles are completed. This corresponds to periodic fortification in about 21 of the 455 cycles or in about 4.6% of the cycles of the circulating acid through the alkylation zone.

These examples are given only to illustrate the effect of diverse factors. Slight variations will always be found, depending, e.g. on the quantity or quality of the make-up or alkylation acid and the alkylation equipment available. For example, although it is not shown in the drawing, the organic and water content of the circu-

TABLE V

Analysis of the Sulfuric Acid Catalyst after 63 Cycles of the Periodic Fortification Process of the Present Invention (Water Content at 1.5%)

| Composition of Alkylation Acid | Acid In | | Acid Out | | Acid Discharged | Fortifying Agent Added | | Acid in Next Cycle | |
|---|---|---|---|---|---|---|---|---|---|
| | weight in lbs. | % by weight | weight in lbs. | % by weight | weight in lbs. | weight in lbs. | % by weight | weight in lbs. | % by weight |
| $H_2SO_4$ | 95.0 | 95.0 | 95.0 | 93.5 | 22.7 | 22.7 | 100* | 95.0 | 95.0 |
| $H_2O$ | 1.5 | 1.5 | 2.0 | 2.0 | .5 | 0 | 0 | 1.5 | 1.5 |
| Organics | 3.5 | 3.5 | 4.6 | 4.5 | 1.1 | 0 | 0 | 3.5 | 3.5 |

*Formed by addition of 2.73 lbs $SO_3$ to 19.97 lbs. of 96.9% $H_2SO_4$ containing 3.1% $H_2O$

EXAMPLE 11

This Example illustrated a preferred embodiment of the present invention wherein the octane number of the product alkylate was improved and the service life of the acid extended. In the 63rd cycle the water in the alkylation acid was returned to 1.5% from 2.0% by applying 13% oleum in one cycle. The organic content in the acid was returned to 8.5% by the method described in Example 10. The build-up rates of water and organic impurities were the same as in Example 10, lating alkylation acid can also be lowered by discharging a portion of the alkylation acid and adding an approximately equal volume of makeup and or alkylation acid from a previous stage. The active alkylation acid from the previous stage could contain various mixtures of organic impurities and water. By replacing the circulating alkylation acid with an approximately equal volume of active alkylation acid or makeup, the frequency of the periodic fortification can be lowered still further. Such modifications are considered within the scope of the process of this invention.

TABLE VI

Analysis of the Sulfuric Acid Catalyst After 63 Cycles of the Periodic Fortification Process of the Present Invention (Water Content at 1.5%)

| Composition of Alkylation Acid | Acid In | | Acid Out | | Acid Discharged | Fortifying Agent Added* | | Acid in Next Cycle | |
|---|---|---|---|---|---|---|---|---|---|
| | weight in lbs. | % by weight | weight in lbs. | % by weight | weight in lbs. | weight in lbs. | % by weight | weight in lbs. | % by weight |
| $H_2SO_4$ | 90.0 | 90.0 | 90.0 | 88.6 | 10.3 | 8.7 | 87.0 | 90.0 | 90.0 |
| $H_2O$ | 1.5 | 1.5 | 2.0 | 2.0 | 0.23 | 0 | 0 | 1.5 | 1.5 |
| Organics | 8.5 | 8.5 | 9.6 | 9.4 | 1.1 | 0 | 0 | 8.5 | 8.5 |
| $SO_3$ | — | — | — | — | — | 1.3 | 13.0 | — | — |

*This is 13% oleum which is added every 63 cycles.

We claim:

1. In a continuous cyclic process for producing alkylate wherein an alkylatable hydrocarbon is contacted with an alkylating agent in an alkylation system under alkylation conditions in the presence of a circulating concentrated sulfuric acid catalyst containing above about 1 weight % and below about 4 weight % of water, the reaction mixture so produced is separated into alkylate and alkylation acid catalyst, a portion of the alkylation acid catalyst is cooled and recycled to the alkylation system, and the water content of the circulatig alkylation acid catalyst is reduced by addition thereto of a sulfur trioxide fortifying agent, the improvement which comprises continuously maintaining the water content in the circulating alkylation acid catalyst in the range of above about 1 weight % and below about 4 weight % by periodically introducing the sulfur trioxide fortifying agent into the cooled portion of said circulating alkylation acid catalyst during less than about 15% of the cycles of the circulating alkylation acid catalyst through the alkylation system.

2. A process as described in claim 1 wherein the improvement further comprises continuously maintaining the water content of the circulating alkylation acid catalyst above about 1.5 weight % and below about 2.5 weight % by periodically introducing the sulfur trioxide fortifying agent into said cooled portion of the circulating alkylation acid catalyst during less than about 3% of the cycles of the circulating alkylation acid catalyst through the alkylation system.

3. A process as described in claim 1 wherein the improvement further comprises extending the duration of each periodic introduction over 2 or 3 successive cycles of the circulation alkylation acid catalyst through the alkylation system.

4. A process as described in claim 1 wherein the improvement further comprises using 13 to 30% oleum as the sulfur trioxide fortifying agent.

* * * * *